US009603967B2

(12) United States Patent
Allen et al.

(10) Patent No.: US 9,603,967 B2
(45) Date of Patent: Mar. 28, 2017

(54) PLACENTAL TISSUE ASSEMBLY

(71) Applicant: Vivex Biomedical Inc., Marietta, GA (US)

(72) Inventors: Roderick Nelson Allen, Gainesville, FL (US); Rebecca Marshall Allen, Gainesville, FL (US)

(73) Assignee: Vivex Biomedical, Inc., Marietta, GA (US)

( * ) Notice: Subject to any disclaimer, the term of this patent is extended or adjusted under 35 U.S.C. 154(b) by 28 days.

(21) Appl. No.: 14/716,131

(22) Filed: May 19, 2015

(65) Prior Publication Data

US 2016/0324797 A1    Nov. 10, 2016

Related U.S. Application Data

(60) Provisional application No. 62/158,879, filed on May 8, 2015.

(51) Int. Cl.
| | | |
|---|---|---|
| *A61L 26/00* | (2006.01) | |
| *A61K 35/50* | (2015.01) | |
| *A61L 15/40* | (2006.01) | |

(52) U.S. Cl.
CPC .......... *A61L 26/0066* (2013.01); *A61K 35/50* (2013.01); *A61L 15/40* (2013.01)

(58) Field of Classification Search
None
See application file for complete search history.

(56) References Cited

U.S. PATENT DOCUMENTS

| | | | |
|---|---|---|---|
| 1,966,942 A * | 7/1934 | Atkinson | B44C 1/1712 |
| | | | 156/230 |
| 6,936,271 B1 | 8/2005 | Oliver et al. | |
| 7,871,646 B2 | 1/2011 | Ghinelli | |
| 8,372,437 B2 | 2/2013 | Daniel | |
| 8,460,715 B2 | 6/2013 | Daniel | |
| 8,597,687 B2 | 12/2013 | Daniel | |
| 2007/0020225 A1 | 1/2007 | Abramson et al. | |
| 2011/0150973 A1 * | 6/2011 | Bowlin | A61F 13/00034 |
| | | | 424/447 |
| 2013/0019569 A1 * | 1/2013 | Epstein | A61F 13/0276 |
| | | | 53/452 |
| 2013/0156863 A1 * | 6/2013 | Tseng | A61K 35/50 |
| | | | 424/583 |
| 2013/0344162 A1 | 12/2013 | Morse et al. | |
| 2014/0050788 A1 | 2/2014 | Daniel et al. | |
| 2014/0178459 A1 * | 6/2014 | Kisak | A61K 9/7061 |
| | | | 424/449 |
| 2014/0302162 A1 | 10/2014 | Morse et al. | |
| 2015/0010506 A1 | 1/2015 | Jansen et al. | |
| 2015/0064274 A1 | 3/2015 | Koob | |
| 2015/0086634 A1 | 3/2015 | Koob et al. | |
| 2015/0231299 A1 * | 8/2015 | Ericson | A61L 15/32 |
| | | | 424/443 |
| 2015/0259119 A1 * | 9/2015 | Duan-Arnold | B65D 77/26 |
| | | | 206/570 |

FOREIGN PATENT DOCUMENTS

| | | |
|---|---|---|
| KR | 20100030031 | 3/2010 |
| KR | 20010100588 | 11/2011 |

OTHER PUBLICATIONS

Ortho-McNeil-Janssen Pharmaceuticals, Inc. Duragesic. Datasheet [online]. Ortho-McNeil-Janssen Pharmaceuticals, Inc., revised 2009 [retrieved on Dec. 28, 2015]. Retrieved from the Internet: <URL: https://dailymed.nlm.nih.gov/dailymed/archives/fdaDrugInfo.cfm?archiveid=11988> pp. 1-37. specif. pp. 1, 3, 29.*

* cited by examiner

*Primary Examiner* — Renee Claytor
*Assistant Examiner* — Sharon M Papciak
(74) *Attorney, Agent, or Firm* — David L. King

(57) ABSTRACT

A placental tissue assembly for treating wounds or surfaces of a patient has one or more layers of placental tissue and a backing material. The one or more layers of placental tissue have a first side and a second side. The backing material is adhered to and covers one of either the first or second sides of the one or more layers of placental tissue to create the assembly. The assembly when applied onto a surface to be treated on the side of the tissue opposite the backing material adheres to the surface with an attachment force greater than an attachment force of the backing material adhered to the first or second side. This allows the backing material to be released leaving the placental tissue affixed to the surface to be treated.

14 Claims, 4 Drawing Sheets

PLACENTAL TISSUE ASSEMBLY

FIELD OF THE INVENTION

This invention relates to a placental tissue assembly for treating wounds or surfaces of a patient. The invention also provides an improved method of applying the placental tissue assembly.

BACKGROUND OF THE INVENTION

Currently, placental tissue is used in various wound and skin tissue treatments to accelerate healing. The placental tissue can be prepared in various forms. One form involves creating layers or membranes of material that has been dried aseptically and packaged, the material being cut into thin squares or rectangles and sterilized for future application on wounds or skin tissue to be treated.

The placental tissue has layers or membranes of chorion and amnion. These layers can be used together or separately or even combined with other layers to construct laminated multiple tissue layers of amnion or chorion or both. The dried layered material when applied is typically rehydrated prior to being applied. The processed placental tissue material when made into a single layer of amnion or chorion is extremely thin and translucent making it difficult to discern sides. An epithelial side is on one side and a stromal side is on an opposite side, distinguishing the two sides is difficult.

U.S. Pat. No. 8,460,715 B2, assigned to Mimedx, teaches the layer or membrane can be embossed with indentations or bumps to indicate a top or bottom surface. In U.S. Pat. No. 8,597,687 B2; also assigned to Mimedx, there is a method of placing an asymmetric label on a portion of at least one side of the tissue graft in order to distinguish one side from another. In that patent, the label is also part of the membrane created by embossing or indenting.

The present invention achieves this ability to discern sides, but in a completely different approach which is unique in that it also greatly facilitates handling of the tissue during treatment so applying the layer is achieved without wrinkling, folds or other issues commonly found in practice. The single layer placental or layer membranes when rehydrated has a tendency to cling to itself like thin plastic film used in wrapping meat, this causes wrinkles and reduces surface contact on the wound to be covered. The present invention, as described herein, solves these issues in a simple and very reliable manner.

SUMMARY OF THE INVENTION

A placental tissue assembly for treating wounds or surfaces of a patient has one or more layers of placental tissue and a backing material. The one or more layers of placental tissue have a first side and a second side. The backing material is adhered to and covers one of either the first or second sides of the one or more layers of placental tissue to create the assembly. The assembly when applied onto a surface to be treated on the side of the tissue opposite the backing material adheres to the surface with an attachment force greater than an attachment force of the backing material adhered to the first or second side. This allows the backing material to be released leaving the placental tissue affixed to the surface to be treated.

Preferably, the backing material has at least a portion extending beyond the side of the tissue. The backing material overlays the one or more layers of placental tissue and extends beyond an outer edge of the one or more layers. The one or more layers have one or more outer edges and the backing material extends beyond the edges.

In one embodiment, the backing material is permeable to liquids and wherein moistening of the backing material reduces the adherence to the first or second side of the one or more layers allowing the backing material to release from the one or more layers. In another embodiment, the backing material is an open mesh or net releasably adhered to one or more layers.

In all embodiments, the assembly is made to be conformable to the surface. The surface can have a shape or a contour to which the one or more layers are to be applied. The placental tissue assembly can have the one or more layers made of amnion layers. It can have a single layer of amnion. Alternatively, the one or more layers can be chorion layers. It can be a single layer of chorion. Alternatively, the one or more layers can be made from micronized placental tissues, wherein the micronized placental tissue is amnion or chorion or combinations thereof. The micronized particles can be layered onto one side of a bioabsorbable membrane or layer similar to grit on sandpaper. The backing material 14 adhered to a side opposite the micronized particles.

The placental tissue assembly of claim 1 wherein the one or more layers are amniotic membranes and the first side or second side not adhered to and opposite the backing material is a stromal side and the side against and adjacent the backing material is an epithelial side. The placental tissue assembly can also have the first or second side opposite the backing material with a releasable peel-off cover attached. The releasable peel-off cover can be cut or formed as two pieces with abutting edges wherein the abutting edges lift from the attached position on bending of the placental tissue assembly to facilitate peeling from the assembly. A method of applying one or more layers of placental tissue to a wound has the steps of providing the one or more layers adhered to a releasable backing material as an assembly; applying the assembly to the wound; and peeling or pulling the releasable backing material from the one or more layers of placental tissue, the one or more layers remaining attached to the wound. The method preferably further has the step of applying the assembly to a wound or surface to be treated and then moistening the backing material to facilitate release from the one or more layers. When the assembly has a peelable cover on a side of the placental tissue opposite the side adhered to the backing material and the method further has the step of removing the cover prior to applying the assembly to the wound.

BRIEF DESCRIPTION OF THE DRAWINGS

The invention will be described by way of example and with reference to the accompanying drawings in which.

DETAILED DESCRIPTION OF THE INVENTION

Figure 1:
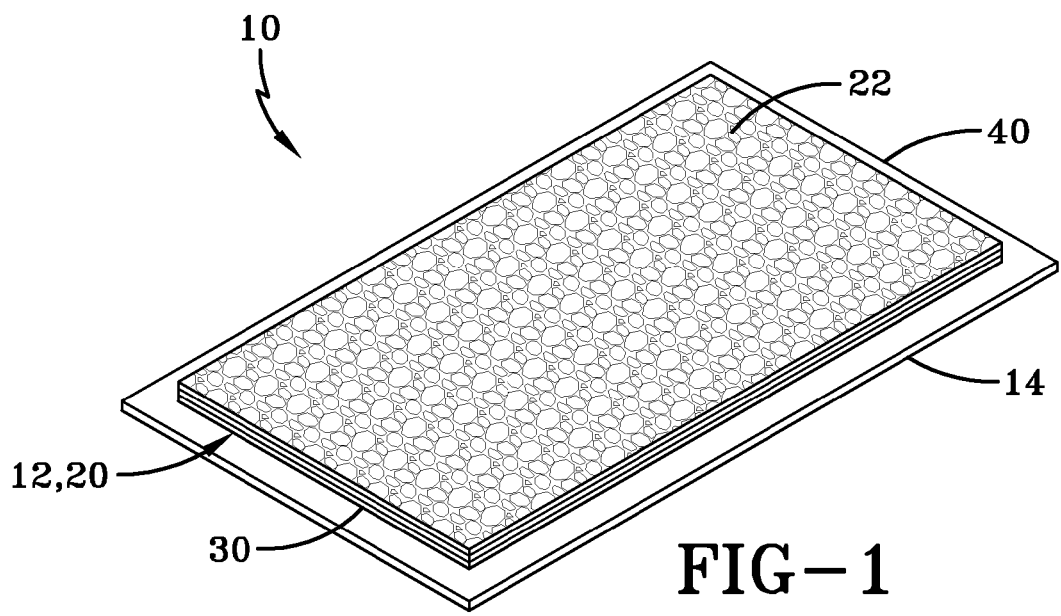
FIG. 1 is a perspective view of the placental tissue assembly made in accordance with the present invention.
Figure 2:
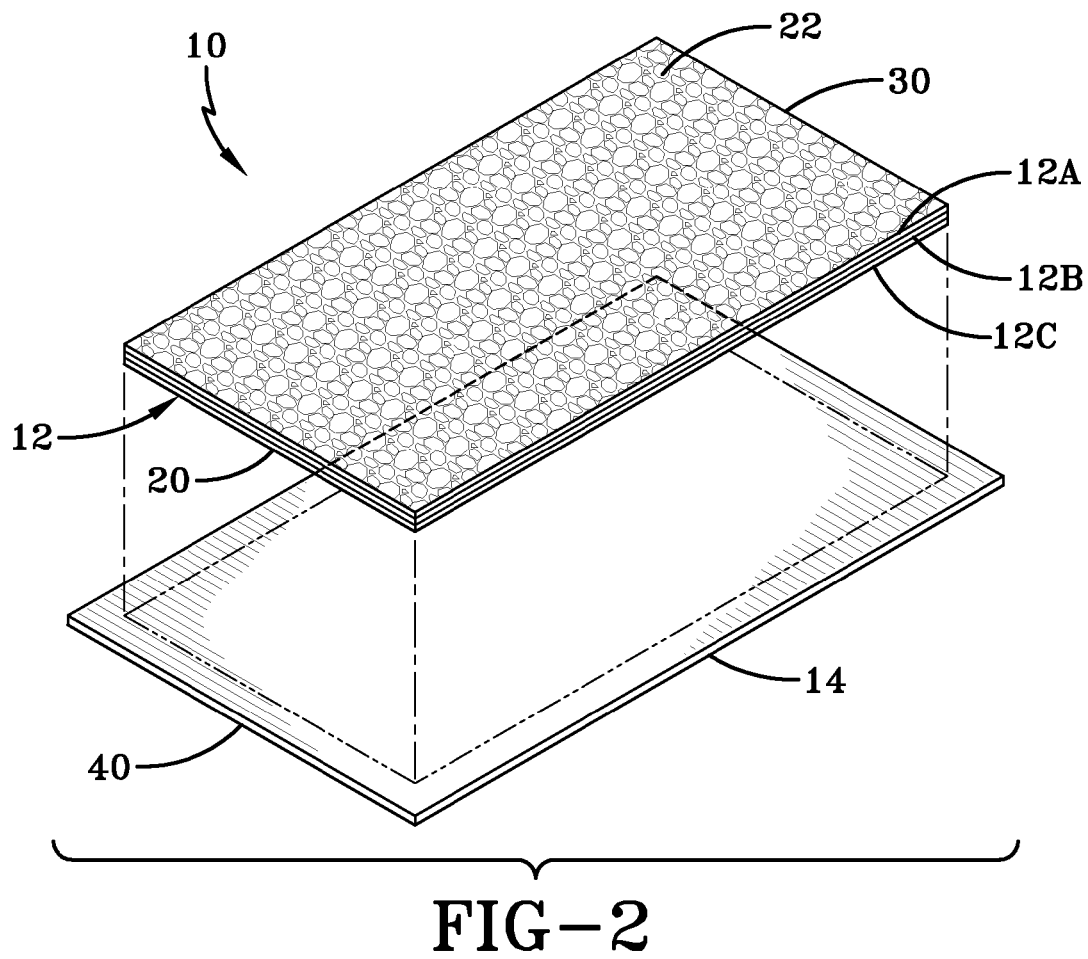
FIG. 2 is an exploded view of the present invention.
Figure 3:
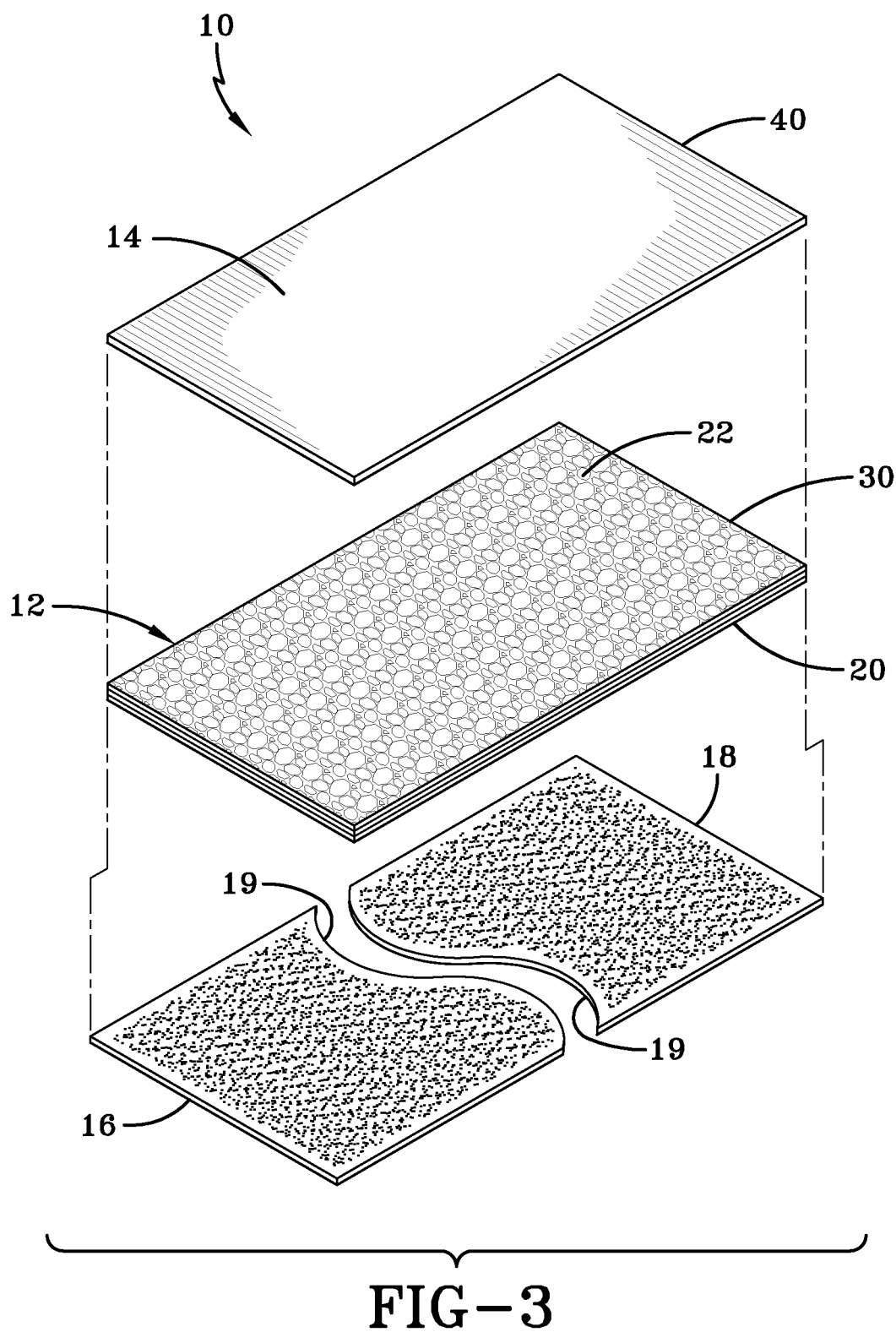
FIG. 3 is an alternative embodiment of the placental tissue having a releasable peel-off cover.

With reference to FIGS. 1 and 2, a perspective view of the placental tissue assembly is shown. The placental tissue assembly 10 has a placental membrane layer 12 affixed to a backing material 14. As shown in FIG. 2, the placental tissue 12 can have one layer 12A or more layers, 12A, 12B, 12C laminated together. The placental tissue has an outer side 20 and an inner side 22. The inner side 22 is adhered to a surface of the backing material 14. The backing material 14 can be sized identical or the same as the placental tissue 12, as shown in FIG. 3. In such a configuration, the backing material 14, after the placental tissue 12 is pressed onto the wound, must be easily released from the placental tissue 12. One way this is accomplished is by moistening the backing material 14 so it can slip relative to the placental tissue 12 and be lifted off. The placental tissue 12 as shown has the one or more layers cut in a rectangular shape that is sized slightly smaller than the rectangular area of the backing material 14. As shown, the placental tissue 12 has boundary edges or edges 30 around the perimeter of the tissue layers 12A, 12B, 12C. The backing material 14 has an edge 40 that extends beyond the edge 30. As shown, it is preferable that at least one edge 40 of the backing material 14 extend beyond the tissue 12. As shown, all four edges 40 are shown overlapping and extending beyond the edges or boundaries 30 of the layers 12A, 12B, 12C. It is understood that the placental tissue 12 can be provided as a single layer of material using 12A only or can be laminated together as illustrated having multiple layers, one or more layers in combination with the backing material 14 are required to make the placental tissue assembly 10.

Figure 2A:
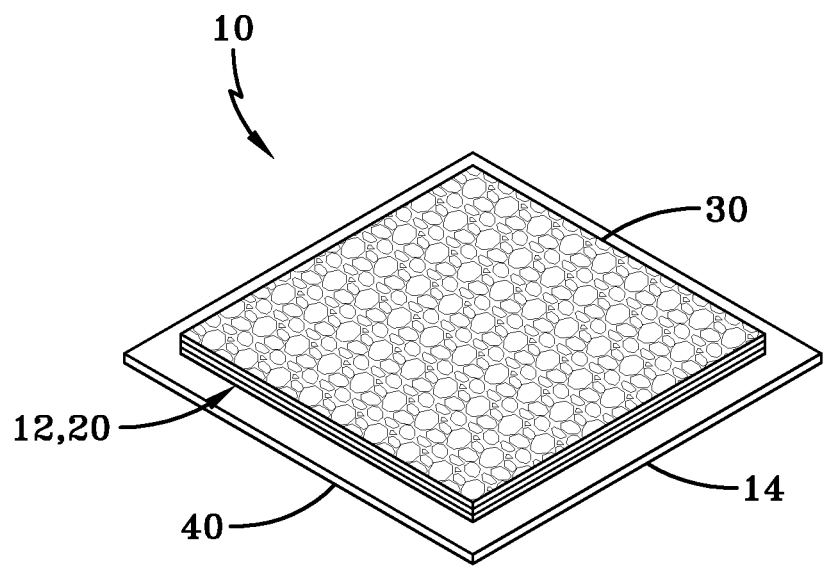
FIG. 2A is the placental tissue assembly shaped as a square assembly.
Figure 2B:
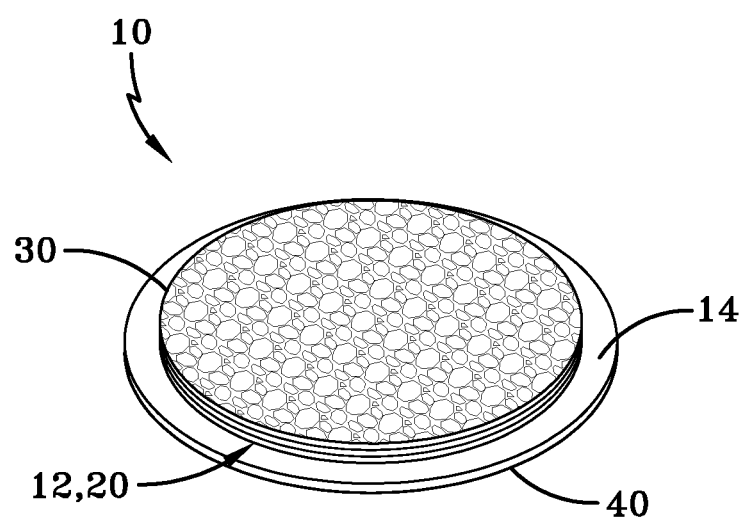
FIG. 2B is the placental tissue assembly shaped as a round or circular assembly.

With reference to FIGS. 2A and 2B, the placental tissue assembly 10 is shown in various exemplary shapes which can be square or circular, as illustrated in FIGS. 2A and 2B respectively. Otherwise, the assembly 10 is identical to that shown in FIGS. 1 and 2. The backing material 14 as shown, has a similar albeit larger shape, but could in fact be in any shape or size to overlap one side 20 or 22 of the placental tissue 12.

In an alternative embodiment, the placental tissue assembly 10 is shown with an additional releasable peelable cover or peel-off cover 16, 18. As shown in FIG. 3, the peel-off cover 16, 18 is cut approximately midway through the surface area along cut abutting edges 19, such that when attached to the side 20, it covers the side 20 and provides additional protection for the tissue 12. The placental tissue on side 22 as illustrated has the backing material 14 adhered to it. The side 20 can either be left unprotected and provided in a sterile package (not illustrated) or can have a releasable peelable cover or peel-off cover 16, 18 as illustrated in FIG. 3. To remove the cover 16, 18; the assembly can be bent slightly so the edges 19 lift from the side 20.

Placental tissue 12 can have an epithelial side and a stromal side, as illustrated. In the present embodiment, envision that the epithelial side is adhered to the backing material 14 and the stromal side is the side that will be attached to a wound or a surface to be treated with the placental tissue 12. The placental tissue 12 can be amnion tissue or can be chorion tissue or can be a combination of chorion and amnion tissue. The placental tissue 12 can also have alternative layers assembled and affixed to the assembly 10 in a lamination, as illustrated in FIG. 2.

In practice, when applying this placental tissue assembly 10 to a wound or surface, it is important that the backing material 14 be sufficiently pliable that the entire assembly 10 can be conformed about the wound or surface to be treated. After the wound or surface has been cleaned, the placental tissue assembly 10 can be laid over the surface and pressed lightly against the wound. In doing so, the assembly 10 is now adhered to the skin surface or wound tissue. Once adhered, it is now possible to wet the placental tissue assembly 10 and with a sponge or damp cloth to moisten the backing material 14 such that the placental tissue 12 attachment to the backing material 14 is reduced dramatically. When this occurs, the backing material 14 can simply be lifted at the edges and the underlying placental tissue 12 will remain firmly attached to the skin or wound tissue. The backing material 14 is a water permeable or absorbable paper or similar composition that will easily peel directly of the wet surface of the placental tissue 12. In this embodiment, the placental tissue 12 is extremely improved in its method of application in that the placental tissue 12 can be a very thin membrane that would otherwise be very difficult to handle in the absence of a backing material. However, the backing material 14 provides enough support that the doctor or surgeon, when applying this placental tissue assembly 10 to the patient, can lay the entire assembly 10 on a wound and when pressed onto the wound, it will maintain an unwrinkled position until released from the backing material 14.

With reference to FIG. 3, an alternative embodiment is shown wherein the releasable or peelable cover 16, 18 is provided. When this occurs, an additional step is required when the placental tissue assembly 10 is taken from the sterile packaging, the nurse or doctor applying the tissue will slightly bend the assembly 10 so that the releasable material releases at the abutting edges 19 on each portion 16, 18 of the peelable cover. When this occurs, the edges 19 will lift slightly from the side 20 and be able to be easily peeled from the placental tissue 12. Once removed, the placental tissue 12 can be applied to the skin or wound as previously discussed.

Figure 4:
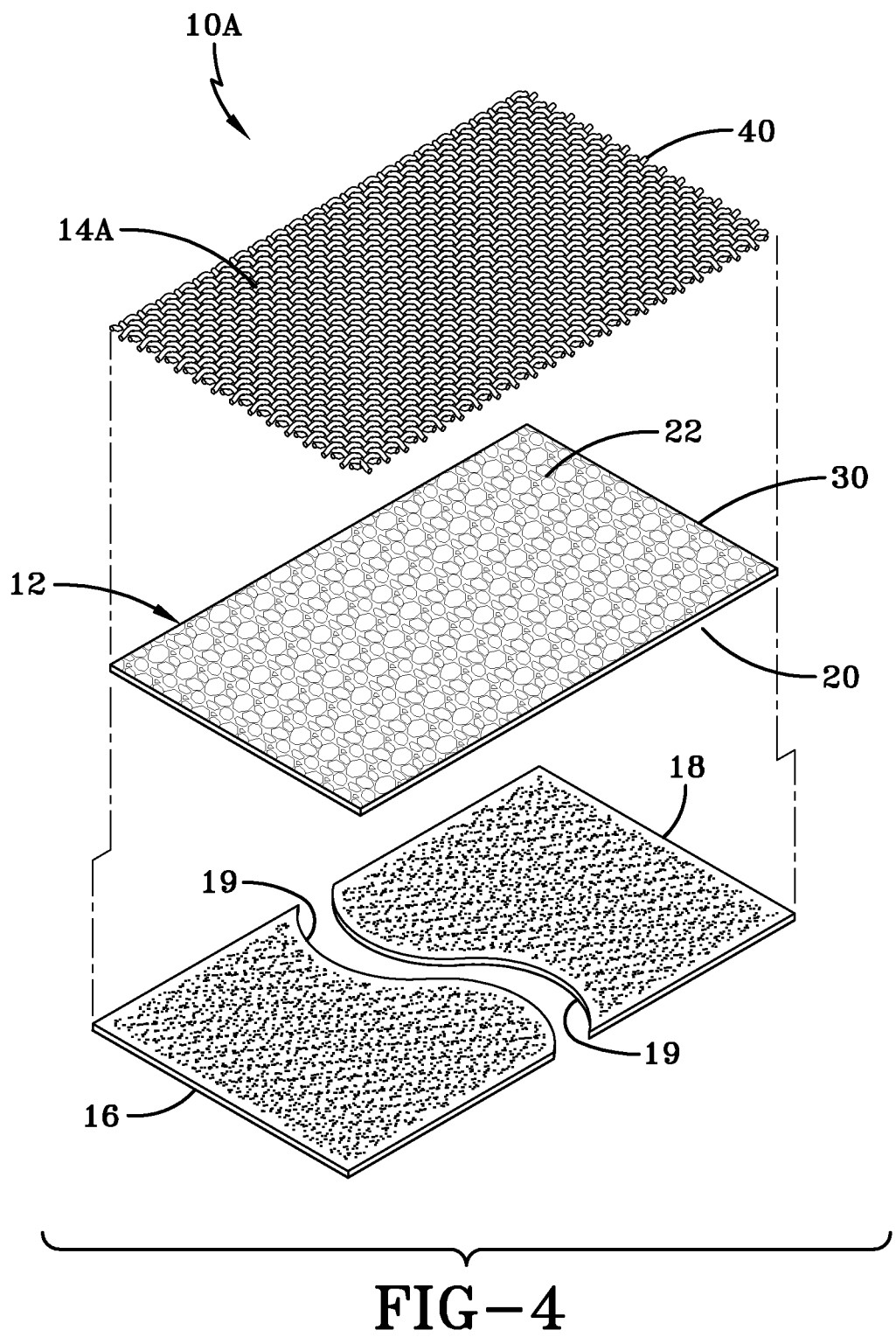
FIG. 4 is another alternative embodiment wherein the backing material is a net or open mesh material.

With reference to FIG. 4, the backing material 14 as previously discussed can be provided as open mesh net 14A that would be adhered to one side of the placental tissue 12. In this embodiment, the open mesh net 14A has minimal contact area with the placental tissue 12, however, provides sufficient support that the placental tissue 12 will not wrinkle or deform during shipping, handling or during any procedure in treatment of a patient. In this embodiment, the adhesive forces between the open mesh net 14A and the placental tissue layer 12 is such that the backing material 14 when formed as an open mesh net 14A can be simply peeled from the placental tissue 12 without requiring any moisture. The procedure for application is very similar to the other embodiments; however there is no need for the additional step of moistening to create a release of backing material 14 from the placental layer 12. In this embodiment, the placental tissue assembly 10 may have the dried layers 12A, 12B, 12C rehydrated prior to attachment to the wound and the open mesh net 14A can be peeled off in either a dried or moistened condition after attachment of the assembly 10 to the wound. In this alternative, the optional peel-off cover 16, 18 can also be used as discussed.

With reference to the drawings, the illustrated thickness of the layers has been greatly exaggerated so the reader can appreciate and discern the features of the laminated placental tissue 12 when used in more than one layer. In reality, these layers have a thickness that approximates a standard sheet of paper which is about 0.05 mm thick. The tissue layer can vary from 0.01 mm to less than 1.0 mm, preferably 0.5 mm or less. The backing material 14 illustrated thickness is similarly exaggerated and is preferably about the thickness of standard paper or about 0.05 mm. It is understood these thicknesses can be varied in any size desired. The open mesh net 14A backing material can be woven and its thickness can be greater, typically 0.5 mm or greater.

Variations in the present invention are possible in light of the description of it provided herein. While certain representative embodiments and details have been shown for the purpose of illustrating the subject invention, it will be apparent to those skilled in this art that various changes and modifications can be made therein without departing from the scope of the subject invention. It is, therefore, to be understood that changes can be made in the particular embodiments described, which will be within the full intended scope of the invention as defined by the following appended claims.

What is claimed is:

1. A placental tissue assembly for treating wounds or surfaces of a patient, the assembly comprising:
   one or more dried layers of placental tissue having a first side and a second side;
   a backing material adhered to and covering one of either the first or second sides of the one or more dried layers of placental tissue to create an assembly wherein the backing material is permeable to liquids and wherein moistening of the backing material wets the adhered surface of the covered first or second side of the one or more dried layers which reduces the adherence to the first or second side of the one or more dried layers allowing the backing material to slip relative to the wetted surface of the placental tissue to release from the one or more layers;
   a releasable peelable or peel-off cover attached to the first or second side opposite the backing material and wherein the releasable peel-off cover is cut or formed as two pieces with abutting edges wherein the abutting edges lift from the attached position on bending of the assembly to facilitate peeling from the assembly prior to applying to the surface to be treated; and
   wherein the assembly when applied onto a wound or surface to be treated on the side of the tissue opposite the backing material adheres to the wound or surface with an attachment force greater than an attachment force of the moistened backing material adhered to the first or second side, thereby allowing the backing material to be released leaving the placental tissue affixed to the surface to be treated.

2. The placental tissue assembly of claim 1 wherein the backing material has at least a portion extending beyond the side of the tissue.

3. The placental tissue assembly of claim 1 wherein the backing material overlays the one or more layers of placental tissue and extends beyond an outer edge of the one or more layers.

4. The placental tissue assembly of claim 3 wherein the one or more layers have one or more outer edges and the backing material extends beyond the edges.

5. The placental tissue assembly of claim 1 wherein the backing material is an open mesh net releasably adhered to one or more layers.

6. The placental tissue assembly of claim 1 wherein the assembly is conformable to the surface, the surface being a shape or a contour to which the one or more layers are to be applied.

7. The placental tissue assembly of claim 1 wherein the one or more layers are amnion layers.

8. The placental tissue assembly of claim 7 wherein the one or more layers is a single layer of amnion.

9. The placental tissue assembly of claim 1 wherein the one or more layers are chorion layers.

10. The placental tissue assembly of claim 9 wherein the one or more layers is a single layer of chorion.

11. The placental tissue assembly of claim 1 wherein the one or more layers is made from micronized placental tissues.

12. The placental tissue assembly of claim 11 wherein the micronized placental tissue is amnion or chorion or combinations thereof.

13. The placental tissue assembly of claim 1 wherein the one or more layers are amniotic membranes and the first side or second side not adhered to and opposite the backing material is a stromal side and the side against the backing material is an epithelial side.

14. A method of applying one or more dried layers of placental tissue to a wound comprises:
   providing the one or more dried layers adhered to a releasable backing material on a first or second side of the one or more dried layers and a releasable or peel-off cover on an opposite side as an assembly;
   removing the cover prior to applying the assembly to the wound;
   applying the assembly to the wound or surface to be treated;
   moistening the backing material, wherein moistening of the moistened backing material wets the adhered surface of the covered first or second side of the one or more dried layers which reduces the adherence to the first or second side of the one or more dried layers allowing the backing material to slip relative to the wetted surface of the placental tissue to release from the one or more layers; and
   peeling or pulling the moistened releasable backing material from the one or more layers, causing the backing material to slip relative to the wetted surface of the placental tissue leaving the one or more layers remaining attached to the wound.

* * * * *